US006696047B2

(12) United States Patent
Scott et al.

(10) Patent No.: US 6,696,047 B2
(45) Date of Patent: Feb. 24, 2004

(54) STABLE ORAL CARE COMPOSITIONS COMPRISING CHLORITE

(75) Inventors: Douglas Craig Scott, Loveland, OH (US); Paula Denise Clymer, Mason, OH (US); Steven Carl Burgess, Sharonville, OH (US); Christine Lula Johnson, Germantown, OH (US); James Carl Grimm, Hamilton, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 10/218,771

(22) Filed: Aug. 14, 2002

(65) Prior Publication Data

US 2003/0129144 A1 Jul. 10, 2003

Related U.S. Application Data

(60) Provisional application No. 60/318,993, filed on Sep. 13, 2001.

(51) Int. Cl.$^7$ .............................. A61K 7/16; A61K 7/20
(52) U.S. Cl. ........................................... 424/53; 424/49
(58) Field of Search ........................................... 424/53

(56) References Cited

U.S. PATENT DOCUMENTS

| | | |
|---|---|---|
| 4,060,600 A | 11/1977 | Vit |
| 4,330,531 A | 5/1982 | Alliger |
| 4,689,215 A | 8/1987 | Ratcliff |
| 4,696,811 A | 9/1987 | Ratcliff |
| 4,786,492 A | 11/1988 | Ratcliff |
| 4,788,053 A | 11/1988 | Ratcliff |
| 4,792,442 A | 12/1988 | Ratcliff |
| 4,793,989 A | 12/1988 | Ratcliff |
| 4,808,389 A | 2/1989 | Ratcliff |
| 4,818,519 A | 4/1989 | Ratcliff |
| 4,837,009 A | 6/1989 | Ratcliff |
| 4,851,213 A | 7/1989 | Ratcliff |
| 4,855,135 A | 8/1989 | Ratcliff |
| 4,861,514 A | 8/1989 | Hutchings |
| 4,886,657 A | 12/1989 | Ratcliff |
| 4,889,714 A | 12/1989 | Ratcliff |
| 4,891,216 A | 1/1990 | Kross et al. |
| 4,925,656 A | 5/1990 | Ratcliff |
| 4,975,285 A | 12/1990 | Ratcliff |
| 4,978,535 A | 12/1990 | Ratcliff |
| 4,986,990 A | 1/1991 | Davidson et al. |
| 5,019,402 A | 5/1991 | Kross et al. |
| 5,110,652 A | 5/1992 | Allaire et al. |
| 5,200,171 A | 4/1993 | Ratcliff |
| 5,281,412 A | 1/1994 | Lukacovic et al. |
| 5,348,734 A | 9/1994 | Ratcliff |
| 5,489,435 A | 2/1996 | Ratcliff |
| 5,618,550 A | 4/1997 | Ratcliff |
| 5,820,822 A | 10/1998 | Kross |
| 6,077,502 A * | 6/2000 | Witt et al. .................... 424/53 |
| 6,132,702 A * | 10/2000 | Witt et al. .................... 424/53 |
| 6,235,269 B1 * | 5/2001 | Witt et al. .................... 424/53 |
| 6,251,372 B1 * | 6/2001 | Witt et al. .................... 424/53 |
| 6,264,924 B1 * | 7/2001 | Witt et al. .................... 424/53 |
| 6,350,438 B1 * | 2/2002 | Witt et al. .................... 424/53 |

FOREIGN PATENT DOCUMENTS

| | | |
|---|---|---|
| DE | 2329753 | 9/1973 |
| DE | 198 54 349 A1 | 11/1998 |
| EP | 287074 A2 | 10/1988 |
| EP | 565134 B1 | 10/1993 |
| GB | 2289841 A | 6/1995 |
| GB | 2290233 A | 12/1995 |
| JP | 054311 | 3/1985 |
| JP | 105610 | 6/1985 |
| WO | WO 89/03179 | 4/1989 |
| WO | WO 95/27472 | 10/1995 |
| WO | WO 96/25916 | 8/1996 |
| WO | WO 98/17195 A1 | 4/1998 |
| WO | WO 99/43294 A1 | 9/1999 |
| WO | WO 02/02063 A2 | 1/2002 |

* cited by examiner

Primary Examiner—Shep K. Rose
(74) Attorney, Agent, or Firm—Emelyn DeLeon Hiland

(57) ABSTRACT

Stable topical oral compositions comprising at least a minimally effective amount of chlorite ion are disclosed, wherein the pH of the final composition is greater than 7, the composition is essentially free of chlorine dioxide, and the composition is stable against loss of chlorite for a period of at least one year under normal storage conditions at about 25° C. or for a period of 3 months under accelerated storage conditions at about 40° C. Preferably the compositions further comprise a flavor system, which is stable against degradation by chlorite. The compositions are formulated as therapeutic rinses, especially mouth rinses, as well as toothpastes, gels, tooth powders, chewing gums, mouth sprays, lozenges (including breath mints), dental implements (such as dental floss and tape), and pet care products.

5 Claims, No Drawings

STABLE ORAL CARE COMPOSITIONS COMPRISING CHLORITE

CROSS REFERENCE TO RELATED APPLICATIONS

This application claims the benefit under 35 USC 119(e) to U.S. application Ser. No. 60/318,993, filed Sep. 13, 2001.

TECHNICAL FIELD

The present invention provides topical oral care compositions, including therapeutic rinses, especially mouth rinses, toothpastes, tooth gels, tooth powders, subgingival gels, chewing gums, mouth sprays, and lozenges (including breath mints), comprising an effective amount of chlorite ion for treating or preventing conditions of the oral cavity, said compositions being stable against loss of chlorite for a period of at least of one year under normal storage conditions at about 25° C. or for a period of at least 3 months under accelerated conditions at about 40° C.

BACKGROUND OF THE INVENTION

Oral malodor, plaque, gingivitis, periodontal disease, and discoloration of the teeth, are all undesirable conditions that affect many people. Malodor of the oral cavity is also known as halitosis or bad breath. It is broadly estimated in the U.S. that 20–90 million individuals have oral malodor. It is generally believed that the cause of this condition is due to the presence of anaerobic bacteria, especially gram-negative anaerobic bacteria, in the mouth. These bacteria will generate volatile sulfur compounds (VSC), which are known to cause breath malodor.

It is recognized in the art that breath malodor can be caused by three chemical compounds. Specifically, these compounds are hydrogen sulfide (H—S—H), methyl mercaptan ($CH_3$—S—H) and dimethyl sulfide ($CH_2$—S—$CH_3$). These compounds result from the degradation of epithelial cells and bacteria in the oral cavity. Specifically, the polypeptide chains of the epithelial cell walls are composed of a series of amino acids including cysteine and methionine which contain sulfur side chains. The death of microorganisms or epithelial cells results in degradation of the polypeptide chains into their amino acid components, especially cysteine and methionine. Cysteine and methionine are precursors to the formation of VSC.

It is also recognized in the art that oral malodor not only comes from the posterior dorsal surface of the tongue but also from periodontal pockets. Furthermore, a person with gingivitis or periodontal disease may have increased oral malodor from disintegrated epithelial cells. Epithelial cells turn over faster if inflammation is present. Therefore, a larger number of these dead epithelial cells remain in the oral cavity and will degrade into malodorous compounds.

In addition VSC will also alter the epithelial barrier, permitting penetration of the barrier by antigenic substances. For example, VSC such as hydrogen sulfide, methyl mercaptan and dimethyl sulfide contribute to the penetration of bacterial toxins through the epithelial barrier into the underlying basal lamina and connective tissue. [A. Rizzo, *Peridontics*, 5: 233–236 (1967); W. Ng and J. Tonzetich, *J. Dental Research*, 63(7): 994–997 (1984); M. C. Solis-Gaffar, T. J. Fischer and A. Gaffar, *J. Soc. Cosmetic Chem.*, 30: 241–247 (1979)] Thereafter, bacterial toxins, bacteria and virus can invade the underlying gingival tissue adjacent to the sulcular space, thereafter invading the underlying connective tissue. A decrease in VSC will decrease the tissue permeability to oral toxins and bacteria.

Systemic entities can contribute to oral malodor as well. These entities include oral carcinomas, diabetes, liver and kidney abnormalities, medications which change the oral environment, ENT problems such as chronic sinusitis, tonsillitis and inflamed adenoids. Gastrointestinal problems do not contribute to chronic oral malodor, although this is a common belief. Evaluation and diagnosis of oral malodor can be achieved with the Halimeter (Interscan). The Halimeter is a gas-analysis sensor that measures the volatile sulfur compounds in breath.

Furthermore, periodontal disease is an undesirable condition, which has widespread occurrence. Periodontal disease is a major cause of tooth loss in adults, beginning as early as age 12. Even by age 15, it is possible that 4 out of 5 persons already have gingivitis and possibly as many as 4 out of 10 have periodontitis.

Periodontal disease affects the periodontium, which is the investing and supporting tissue surrounding a tooth (i.e., the periodontal ligament, the gingiva, and the alveolar bone). Gingivitis and periodontitis are inflammatory disorders of the gingiva and the deeper periodontal tissues, respectively.

It is well accepted that periodontal disease is associated with the accumulation of plaque on the teeth. The teeth are coated with a salivary proteinaceous material (pellicle) and thereafter bacteria adhere to this coating. Gingivitis occurs from the dental plaque, and periodontitis is caused by the infection spreading to the periodontal pocket or space between the gingiva and the tooth root.

Furthermore, consumers are very interested in making their teeth whiter. Consumers consider people with whiter teeth as having more personal confidence and better social acceptance.

Teeth comprise both an inner dentin layer and an outer hard enamel layer. The enamel layer protects the inner dentin layer and live tissue and serves as the contact surface for mastication of solid food. The enamel layer is generally translucent and slightly off-white in color. It is also considered porous since the hydroxy apatite crystals that comprise the enamel form microscopic hexagonal rods or prisms having microscopic pores or channels between them. As a result of this porous structure, staining agents and discoloring substances, such as antibiotics, foods containing coloring materials, coffee, cola, tea, tobacco, etc., can permeate the enamel and change its surface to appear yellow or brownish in color.

While good oral hygiene, as achieved by brushing the teeth with a cleansing dentifrice, may help reduce the incidence of stain, gingivitis, plaque, periodontal disease, and/or breath malodor, it does not necessarily prevent or eliminate their occurrence. Microorganisms contribute to both the initiation and progression of gingivitis, plaque, periodontal disease, and/or breath malodor. Thus, in order to prevent or treat these conditions, these microorganisms must be suppressed by some means other than simple mechanical scrubbing. In addition, simple mechanical scrubbing will not be entirely effective to remove all stain types and/or whiten the teeth.

Towards this end, a great deal of research has been aimed at developing therapeutic compositions and methods of treating the above conditions that are effective in suppressing microorganisms. Also, research has been aimed at developing effective whitening compositions. Some of this research has focused on oral care compositions and methods comprising chlorine dioxide or compounds that generate chlorine dioxide. Chlorine dioxide is a very strong oxidant and is known as a broad spectrum antimicrobial agent.

There has been disclosure in the art of compositions and methods that use chlorine dioxide for the treatment of various oral care conditions. Most of these references teach that the delivery of chlorine dioxide is essential to provide efficacy. For example, U.S. Pat. No. 4,689,215 issued Aug. 25, 1987; U.S. Pat. No. 4,837,009 issued Jun. 6, 1989; U.S. Pat. No 4,696,811, issued Sep. 29, 1987; U.S. Pat. No. 4,808,389 issued Feb. 28, 1989; U.S. Pat. No. 4,786,492 issued Nov. 22, 1988; U.S. Pat. No. 4,788,053 issued Nov. 29, 1988; U.S. Pat. No. 4,792,442 issued Dec. 20, 1988; U.S. Pat. No. 4,818,519 issued Apr. 4, 1989; U.S. Pat. No. 4,851,21 issued Jul. 25, 1989; U.S. Pat. No. 4,855,135 issued Aug. 8, 1989; U.S. Pat. No. 4,793,989 issued Dec. 27, 1988; U.S. Pat. No. 4,886,657 issued Dec. 12, 1989; U.S. Pat. No. 4,889,714 issued Dec. 26, 1989; U.S. Pat. No. 4,925,656 issued May 15, 1990; U.S. Pat. No. 4,975,285 issued Dec. 4, 1990; U.S. Pat. No. 4,978,535 issued Dec. 18, 1990; U.S. Pat. No. 5,200,171 issued Apr. 6, 1993; U.S. Pat. No. 5,348,734 issued Sep. 20, 1994; U.S. Pat. No. 5,618,550 issued Apr. 8, 1997, and U.S. Pat. No. 5,489,435 issued Feb. 6, 1996, all to Perry A. Ratcliff, teach oral care compositions and methods of treatment using stabilized chlorine dioxide.

Additional references teach the generation and delivery of chlorine dioxide with activator compounds such as protic acids, reducing sugar activators, etc. and include: U.S. Pat. No. 5,281,412, Lukacovic et al., issued Jan. 25, 1994, The Procter & Gamble Co.; U.S. Pat. No. 5,110,652, Kross et al., issued Mar. 31, 1992, Alcide Corporation; U.S. Pat. No. 5,019,402, Kross et al., issued May 28, 1991, Alcide; U.S. Pat. No. 4,986,990, Davidson et al., issued Jan. 22, 1991, Alcide; U.S. Pat. No. 4,891,216, Kross et al., issued Jan. 2, 1990, Alcide; U.S. Pat. No. 4,330,531, Alliger, issued May 18, 1982; DE 2,329,753, published Dec. 13, 1973, National Patent Development Corp.; EP 287,074, Kross et al., published Oct. 19, 1988, Alcide; EP 565,134, Kross et al., published Oct. 13, 1993, Alcide; and WO/95/27472, Richter, published Oct. 19, 1995.

Additional disclosures relating to chlorine dioxide compositions include: GB 2,289,841, Mehmet, published Jun. 12, 1995, Janina International; GB 2,290,233, Drayson et al., published Dec. 20, 1995, Medical Express Limited; WO 96/25916, Van Den Bosch et al., published Aug. 29, 1996, Diamond White; JP 054,311, Tsuchikura, published Mar. 28, 1985; JP 105,610, Tsuchikura, published Jun. 11, 1985; and WO/89/03179, Partlow et al., published Apr. 20, 1989, New Generation Products.

The compositions and methods of treatment that have focused on the delivery of chlorine dioxide for efficacy have various drawbacks. For example, compositions comprising chlorine dioxide can exhibit aesthetic disadvantages such as "chlorine" (e.g., swimming pool) taste and smell. In addition, due to the strong oxidizing capability of chlorine dioxide, compositions comprising chlorine dioxide may have certain stability disadvantages, especially in oral care formulations.

In contrast to the above references dealing with delivery of chlorine dioxide, the delivery of chlorite ion itself to the oral cavity to provide efficacy against various oral care conditions has been the subject of commonly-assigned U.S. application Ser. No. 09/032,237 (issued as U.S. Pat. No. 6,251,372); Ser. No. 09/032,234 (issued as U.S. Pat. No. 6,132,702); Ser. No. 09/032,238 (issued as U.S. Pat. No. 6,077,502), all filed Feb. 27, 1998 and Ser. No. 09/607,242, filed Jun. 30, 2000. These applications relate to compositions for the delivery of chlorite ion to the oral cavity for efficacy, wherein the compositions are specifically formulated to avoid or minimize the production of chlorine dioxide or chlorous acid. Specifically, these oral care compositions comprising chlorite ion, have relatively alkaline pHs, i.e., above 7, whereby no (or only very low levels of) chlorine dioxide or chlorous acid is generated or is present in the oral care composition at the time of use. These compositions and methods are effective even though no (or only very low levels of) chlorine dioxide or chlorous acid is generated or is present in these compositions.

However, formulating aqueous oral compositions comprising chlorite even at alkaline pHs whereby generation of chlorine dioxide or chlorous acid is minimized or avoided, still presents significant difficulties for the formulator. It is well known that chlorite is unstable in most situations and conditions, and is strongly affected by light and heat, as well as pH, organics and trace metal ions. Even at alkaline pH, there may be a sufficient concentration of $H^+$ ions to start conversion of the chlorite ion to chlorine dioxide, especially at elevated temperatures. As more chlorine dioxide is generated, the aqueous composition becomes more acidic and the rate of conversion of chlorite to chlorine dioxide increases. Further, chlorite ion itself is fairly chemically reactive and may be involved in degradation of excipients such as those commonly used in oral care compositions, in particular flavoring agents.

For example, U.S. Pat. No. 4,861,514 issued to Hutchings discloses aqueous disinfectant compositions containing sodium chlorite, wherein the chlorite interacts with an initiator specifically to form chlorine dioxide, which is the intended disinfecting and sterilizing agent. The compositions as initially prepared have a basic pH. However, the compositions, after reaching equilibrium, have pH values that are slightly basic, neutral, or somewhat acidic, although an organic or inorganic acid constituent such as described in the other patents is not present. Hutchings discloses several classes of initiators suitable to form chlorine dioxide from chlorite including (1) thickeners such as hydroxyalkyl cellulose having from 2 to about 5 carbons in the alkyl group, alkali metal alginates, xanthan gum, carrageenan, and agar; (2) dyes; (3) compounds having an aldehyde or acetal substitutent group; (4) perfume materials that have aldehyde and acetal substituent groups considered above under (3) or other substituent groups, such as the carbonyl group in ketones; the hydroxyl group in alcohols; the acyl group in esters; the C=O groups in lactones; nitrile groups, and the oxy moiety in ethers; and (5) reducing sugars.

The present inventors have now discovered that aqueous oral compositions containing chlorite can be formulated, which are stable against loss of chlorite via conversion to chlorine dioxide as well as against degradation of other composition ingredients such as flavors and sweeteners. In addition to maintaining the intended level of chlorite ion for efficacy, it is particularly important for oral care compositions that the flavor components do not degrade as consumer acceptability of the product is significantly influenced by the flavor and taste of the product. The stability of certain flavor agents in the presence of chlorite is particularly unexpected since these agents have chemical structures similar to the perfume ingredients taught by Hutchings to initiate chlorine dioxide formation by reaction with chlorite.

SUMMARY OF THE INVENTION

The present invention provides topical oral care compositions, including therapeutic rinses, especially mouth rinses, toothpastes, tooth gels, tooth powders, subgingival gels, chewing gums, mouth sprays, and lozenges (including breath mints), comprising an effective amount of chlorite ion, preferably a minimally effective amount, for treating or preventing conditions of the oral cavity, said compositions being stable against significant loss of chlorite for a period of at least one year under normal storage conditions of about 25° C. or for a period of at least three months under accelerated conditions at about 40° C. Specifically, the present compositions comprise (a) from about 0.02% to about 6.0%, by weight of the final composition, of chlorite ion; and (b) a pharmaceutically-acceptable topical, oral carrier comprising solid or liquid excipients and diluents, which are capable of being commingled with chlorite without substantially interacting with chlorite in a manner which would substantially reduce the stability of the composition;

wherein the composition is essentially free of chlorine dioxide; and the pH of the final composition is greater than 7. Preferably, the pH of the final composition is greater than about 8, even more preferably from about 9 to about 12. Preferably, the composition comprises a flavor system comprising flavoring and sweetening agents selected from menthol, eucalyptol, menthone, menthyl acetate, dihydroanethole, N-ethyl-p-menthan-3-carboxamide (WS-3), N,2,3-trimethyl-2-isopropylbutanamide (WS-23), saccharin, sucralose, and mixtures thereof.

These and other features, aspects, and advantages of the present invention will become evident to those skilled in the art from the detailed description which follows.

DETAILED DESCRIPTION OF THE INVENTION

While the specification concludes with claims, which particularly point out and distinctly claim the invention, it is believed the present invention will be better understood from the following description.

All documents cited are, in relevant part, incorporated herein by reference; the citation of any document is not to be construed as an admission that it is prior art with respect to the present invention.

All percentages and ratios used herein are by weight of the specific oral composition and not of the overall oral formulation that is delivered, unless otherwise specified. All measurements are made at 25° C., unless otherwise specified.

Herein, "comprising" means that other steps and other ingredients which do not affect the end result can be added. This term encompasses the terms "consisting of" and "consisting essentially of".

By "topical oral care composition" or "oral composition" as used herein is meant a product which is not intentionally swallowed for purposes of systemic administration of therapeutic agents, but is retained in the oral cavity for a sufficient time to contact substantially all of the dental surfaces and/or oral mucosal tissues for purposes of oral activity.

The oral composition of the present invention may be in the form of a dentifrice, toothpaste, tooth powder, topical oral gel, mouthrinse, denture product, mouthspray, lozenge, oral tablet, or chewing gum.

The term "dentifrice", as used herein, means paste, gel, or liquid formulations unless otherwise specified. The dentifrice composition may be a single phase composition or may be a combination of two or more dentifrice compositions. The dentifrice composition may be in any desired form, such as deep striped, surface striped, multilayered, having the gel surrounding the paste, or any combination thereof. Each dentifrice composition in a dentifrice comprising two or more separate dentifrice compositions may be contained in a physically separated compartment of a dispenser and dispensed side-by-side.

The term "dispenser", as used herein, means any pump, tube, or container suitable for dispensing the oral compositions herein. A preferred dispenser is one having the capability to dispense metered amounts of product, such as disclosed in commonly assigned U.S. Provisional Application No. 60/296,086, file Jun. 5, 2001.

By the term "carrier", as used herein, is meant a suitable vehicle including excipients and diluents, which are pharmaceutically acceptable and can be used to apply the present compositions in the oral cavity. Such materials include fluoride ion sources, additional anticalculus agents, buffers, abrasive polishing materials, alkali metal bicarbonate salts, thickening materials, humectants, water, surfactants, titanium dioxide, flavor system, sweetening agents, coloring agents, and mixtures thereof.

By "diseases or conditions of the oral cavity," as used herein, is meant diseases of the oral cavity including periodontal disease, gingivitis, periodontitis, periodontosis, adult and juvenile periodontitis, and other inflammatory conditions of the tissues within the oral cavity, plus caries, necrotizing ulcerative gingivitis, and other conditions such as herpetic lesions, and infections that may develop following dental procedures such as osseous surgery, tooth extraction, periodontal flap surgery, dental implantation, and scaling and root planing. Also specifically included are dentoalveolar infections, dental abscesses (e.g., cellulitis of the jaw; osteomyelitis of the jaw), acute necrotizing ulcerative gingivitis (i.e., Vincent's infection), infectious stomatitis (i.e., acute inflammation of the buccal mucosa), and Noma (i.e., gangrenous stomatitis or cancrum oris). Oral and dental infections are more fully disclosed in Finegold, Anaerobic Bacteria in Human Diseases, chapter 4, pp 78–104, and chapter 6, pp 115–154 (Academic Press, Inc., NY, 1977). The compositions and methods of treatment of the present invention are particularly effective for treating or preventing periodontal disease (gingivitis and/or periodontitis) and resulting breath malodor.

By "safe and effective amount" as used herein is meant an amount of a chlorite ion, high enough to significantly (positively) modify the condition to be treated, but low enough to avoid serious side effects (at a reasonable benefit/risk ratio), within the scope of sound medical/dental judgment. The safe and effective amount of a chlorite ion, will vary with the particular condition being treated, the age and physical condition of the patient being treated, the severity of the condition, the duration of treatment, the nature of concurrent therapy, the specific form (i.e., salt) of the chlorite source employed, and the particular vehicle from which the chlorite ion is applied.

By "essentially free of chlorous acid or chlorine dioxide" as used herein is meant a composition which comprises very low levels, e.g. less than about 2 ppm, preferably less than about 1 ppm of chlorine dioxide or chlorous acid, using known analytical methods for measuring chlorine dioxide or chlorous acid including highly specific electron spin resonance (ESR) spectroscopy.

The present invention provides compositions for delivery of chlorite ion to the oral cavity for efficacy, said compositions being specifically formulated to be stable against degradation of chlorite to chlorine dioxide and against degradation of other composition excipients, particularly flavoring ingredients. The present compositions maintain the level of chlorite ion required for efficacy for at least 1 year under normal storage conditions at about 25° C. or for at least 3 months under accelerated storage conditions at 40° C., wherein no (or only very low levels of) chlorine dioxide is generated or is present in the oral care compositions at the time of use. Moreover, the present compositions are stable against degradation of flavor ingredients, which is unexpected and surprising based on the known reactivity of chlorite with structurally similar chemicals such as perfume ingredients containing aldehyde, acetal, carbonyl group in ketones and lactones; hydroxyl group in alcohols; acyl group in esters; nitrile groups, and oxy moiety in ethers. Aqueous compositions according to the present invention are formulated at a basic pH and do not undergo a substantial change in pH during storage. The compositions also do not exhibit the penetrating and unpleasant odor of chlorine dioxide, which would tend to further alter the flavor characteristics of the product.

In one aspect the present invention relates to topical oral care compositions for humans and other animals, including therapeutic rinses, especially mouth rinses, as well as toothpastes, tooth gels, tooth powders, non-abrasive gels (including subgingival gels), chewing gums, mouth sprays, lozenges (including breath mints), dental implements (such as dental floss and tape), and pet care products (including nutritional supplements, food, drinking water additives, chews or toys), comprising:

(a) from about 0.02% to about 6.0%, by weight of the final composition, of chlorite ion; and (b) a pharmaceutically-acceptable topical, oral carrier comprising solid or liquid excipients and diluents, which are capable of being commingled without substantially interacting with chlorite in a manner which would substantially reduce the composition's stability; wherein the composition is essentially free of chlorine dioxide; the pH of the final composition is greater than 7, and the composition is stable with respect to loss of chlorite for a period of at least one year under normal storage conditions at about 25° C. or for a period of at least three months under accelerated storage conditions at about 40° C. The compositions are further essentially free of chlorous acid, hypochlorite ions or hypochlorite salts. Preferably the pH of the composition is greater than about 8, even more preferably from about 9 to about 12. Preferably, the pharmaceutically-acceptable topical, oral carrier comprises a flavor system comprising flavoring and sweetening agents selected from menthol, eucalyptol, menthone, menthyl acetate, dihydroanethole, N-ethyl-p-menthan-3-carboxamide (WS-3), N,2,3-trimethyl-2-isopropylbutanamide (WS-23), saccharin, sucralose and mixtures thereof.

The compositions of the present invention can be dual phase compositions or single phase compositions. The dual phase compositions comprise a first phase and a second phase:

(a) the first phase comprising chlorite ion; and (b) the second phase comprising a pharmaceutically-acceptable topical, oral carrier and comprising no chlorite.

These dual phase compositions comprise two phases, wherein chlorite ion is placed in a first phase which is to be kept separate from the second phase. The first phase comprising chlorite ion can additionally comprise pharmaceutically-acceptable topical, oral carriers which are compatible with chlorite ion. Preferably the first phase, in addition to chlorite, comprises one (or more) compatible binder, buffer and/or preservative. Preferably, the second phase, which comprises no chlorite, comprises flavorant, surfactant, fluoride ion, humectant, and/or abrasive.

Normally, each phase in these two phase compositions, is in a separate container or in a single container with two chambers. Prior to use of dual phase composition by the consumer, the two phases are combined by coextrusion of the two separate phases, preferably at a 1:1 volume to volume ratio, and the composition is preferably used immediately after preparation, i.e. within about 5 minutes.

The two phases, however, can be combined from about 1 minute to about 1 hour before use, or during the use of the composition.

Dual phase containers are disclosed in U.S. Pat. No. 5,052,590, Ratcliffe, issued Oct. 1, 1991 and U.S. Pat. No. 4,330,531, Alliger, issued May 18, 1982.

In another embodiment; chlorite is substantially anhydrous until just prior to use. For example, preparing a mouth rinse solution just prior to use by dissolving in water, a substantially anhydrous concentrate of chlorite, to the necessary concentration for use in the method of treatments of the present invention.

The pH of the final composition (either a single phase or dual phase composition) of the present invention is greater than 7, preferably from about 8 to 12; still more preferably the pH is from 9 to 11.5.

For dual phase compositions the pH is measured after the two phases are mixed together, and is not based on the pH of a single phase prior to mixing.

The pH of the final dentifrice composition is measured from a 3:1 aqueous slurry of toothpaste, e.g. 3 parts water to 1 part toothpaste.

Optionally, the present compositions further comprise one or more additional therapeutic agents selected from the group consisting of: antimicrobial/antiplaque agents, anti-inflammatory agents (including cyclo-oxygenase inhibitors and lipoxygenase inhibitors), H2-antagonists, metalloproteinase inhibitors, cytokine receptor antagonists, lipopolysaccharide complexing agents, tissue growth factors, immunostimulatory agents, cellular redox modifiers (antioxidants), biofilm inhibiting agents, analgesics, hormones, vitamins, and minerals. It is recognized that in certain forms of therapy, combinations of therapeutic agents in the same delivery system may be useful in order to obtain an optimal effect. The chlorite ion may be combined with one or more of such agents in a single delivery system to provide combined effectiveness. These additional therapeutic agents must of course be compatible with chlorite and not cause stability problems.

The present compositions comprise essential components, as well as optional components. The essential and optional components of the compositions of the present invention are described in the following paragraphs.

Chlorite Ion Source

Chlorite ion is an essential ingredient in the compositions and methods of the present invention. The chlorite ion can come from any type of chlorite salt. Examples include alkali metal chlorites, alkaline earth metal chlorites, and any other transition metals, inner transition metal chlorites and/or polymeric salts. Water soluble chlorite salts are preferred. Examples of suitable metal chlorites include calcium chlorite, barium chlorite, magnesium chlorite, lithium chlorite, sodium chlorite and potassium chlorite. Sodium chlorite and potassium chlorite are preferred. Sodium chlorite is particularly preferred. Mixtures of two or more sources of chlorite may also be used.

The concentration of chlorite ion in the composition of the present invention depends on the type of composition (e.g., toothpaste, mouth rinse, lozenge, gum, etc.) used to apply the chlorite ion to the gingival/mucosal tissue and/or the teeth, due to differences in efficiency of the compositions contacting the tissue and teeth, and due also to the amount of the composition generally used. The concentration may also depend on the disease or condition being treated.

For dentifrice compositions of the present invention, the level of chlorite ion is greater than about 0.02%, preferably greater than about 0.4%, and more preferably from about 0.5% to about 3% by weight of the final composition.

For mouthrinse compositions of the present invention, the level of chlorite ion is greater than about 0.02%, preferably from about 0.075% to about 0.50% and more preferably from about 0.10% to about 0.30%, by weight of the final composition.

Mouth sprays preferably have chlorite ion concentrations from about 0.15% to about 5%, with from about 0.2% to about 4% more preferred, with from about 0.5% to about 3.5%, by weight of the composition, even more preferred.

For lozenge or breath mint compositions of the present invention, the amount of chlorite ion is from about 0.1 mg to about 12 mg, preferably from about 1 mg to about 6 mg, per unit of product.

For gum compositions of the present invention, the amount of chlorite ion is from about 0.1 mg to about 12 mg, preferably from about 1 mg to about 6 mg, per unit of product.

For methods of treating or preventing gingivitis, preferably the compositions comprise from about 0.1% to about 6%, of chlorite ion, by weight of the composition.

In the context of breath odor elimination or reduction, the compositions and methods of the present invention provide long-lasting breath protection, e.g. greater than about 3 hours.

For methods of treating or preventing oral malodor, and for breath protection lasting greater than about 3 hours, preferably the compositions comprise from about 0.04% to about 6%, of chlorite ion, by weight of the composition.

Chlorite salts are available from various suppliers usually as sodium chlorite. Sodium chlorite is commercially available as a technical grade powder or flake, and as an aqueous liquid concentrate in a range of concentrations. Example of sources of sodium chlorite include: sodium chlorite available from Aragonesas and from Vulcan. These sources generally have no more than 4% sodium chlorate as well.

Preferably, the source of chlorite ion has high purity, e.g. 70% or greater. Furthermore, preferably the compositions of the present invention are essentially free of hypochlorite metal salt or hypochlorite ion, dichloroisocyanurate, or salts thereof.

Preferably, the level of chlorite ion is measured by gradient separation of inorganic and organic acid anions using Ion Pac ASII exchange column, available from Dionex Corporation, Sunnyvale, Calif.

The final compositions of the present invention are essentially free or comprise very low levels of chlorine dioxide or chlorous acid (have less than about 2 ppm, preferably less than about 1 ppm of chlorine dioxide or chlorous acid).

For dual phase compositions the level of chlorine dioxide or chlorous acid is measured within about 2 to 3 minutes after the two phases are mixed together.

Analytical methods to measure the levels of chlorine dioxide or chlorous acid in the compositions of the present invention are known in the art. For example, L. S. Clesceri, A. E. Greenberg, and R. R. Trussel, *Standard Methods for the Examination of Water and Wastewater*, 17$^{th}$ ed., American Public Health Association, Washington, D.C., 1989, pp. 4–75 through 4–83; E. M. Aieta, P. V. Roberts, and M. Hernandez, *J.Am. Water Works Assoc.* 76(1), pp. 64–70 (1984); J. D. Pfaff and C. A. Brockhoff, *J. Am. Water Works Assoc.* 82(4), pp. 192–195 (1990); G. Gordon, W. J. Cooper, R. G. Rice, and G. E. Pacey, *J. Am. Water Works Assoc.* 80(9), pp. 94–108 (1988); D. L. Harp, R. L. Klein, and D. J. Schoonover, *J. Am. Water Works Assoc.* 73(7), pp. 387–389 (1981); G. Gordon, W. J. Cooper, R. G. Rice, and G. E. Pacey, *Am. Water Works Assoc. Res. Foundation*, Denver, Colo., 1987, pp. 815; E, Lynch, et al., *Free Radical Research*, 26(3) 209–234 (1997), R. S. Keyes and A. M. Bobst in *Biological Magnetic Resonance*, 14, pp. 283–338 (1998).

Pharmaceutically-Acceptable Oral Carriers

By "pharmaceutically-acceptable oral carrier" or "pharmaceutically-acceptable excipient," as used herein, is meant one or more compatible solid or liquid filler diluents or encapsulating substances which are suitable for topical, oral administration. By "compatible," as used herein, is meant that the components of the composition are capable of being commingled without interaction in a manner which would substantially reduce the stability of the composition, and/or aesthetic acceptability and/or efficacy for treating or preventing breath malodor, plaque, gingivitis, periodontal disease and for whitening teeth, according to the compositions and methods of the present invention.

Compatible carriers or excipients for use in the present compositions (i.e., dentifrices including gels and gels for subgingival application, mouth rinses, mouth sprays, chewing gums, and lozenges including breath mints) are more fully described hereinafter.

The choice of a carrier to be used is basically determined by the way the composition is to be introduced into the oral cavity. If a toothpaste (including tooth gels, etc.) is to be used, then a "toothpaste carrier" is chosen from those disclosed in, e.g., U.S. Pat. No. 3,988,433, to Benedict, (e.g., abrasive materials, sudsing agents, binders, flavoring and sweetening agents, etc.). Components of the carrier must of course be compatible with chlorite. If a mouth rinse is to be used, then a "mouth rinse carrier" is chosen, as disclosed in, e.g., U.S. Pat. No. 3,988,433 to Benedict (e.g., water, flavoring and sweetening agents, etc.). Similarly, if a mouth spray is to be used, then a "mouth spray carrier" is chosen or if a lozenge is to be used, then a "lozenge carrier" is chosen (e.g., a candy base), candy bases being disclosed in, e.g., U.S. Pat. No. 4,083,955, to Grabenstetter et al.; if a chewing gum is to be used, then a "chewing gum carrier" is chosen, as disclosed in, e.g., U.S. Pat. No. 4,083,955, to Grabenstetter et al., (e.g., gum base, flavoring and sweetening agents). If a sachet is to be used, then a "sachet carrier" is chosen (e.g., sachet bag, flavoring and sweetening agents). If a subgingival gel is to be used (for delivery of actives into the periodontal pockets or around the periodontal pockets), then a "subgingival gel carrier" is chosen as disclosed in, e.g. U.S. Pat. No. 5,198,220, issued Mar. 30, 1993, and U.S. Pat. No. 5,242,910, issued Sep. 7, 1993, both to Damani. Carriers suitable for the preparation of compositions of the present invention are well known in the art. Their selection will depend on secondary considerations like taste, cost, and shelf stability, etc.

The compositions of the present invention may be in the form of non-abrasive gels, including subgingival gels, which may be aqueous or non-aqueous. Aqueous gels generally include a thickening agent (from about 0.1% to about 20%), a flavoring agent (from about 0.04% to about 2%), a sweetening agent (from about 0.1% to about 3%), a compatible coloring agent (from about 0.01% to about 0.5%), and the balance water. The compositions may comprise an anticaries agent (from about 0.05% to about 0.3% as fluoride ion), and an anticalculus agent (from about 0.1% to about 13%).

Preferred compositions of the subject invention may be in the form of dentifrices, such as toothpastes, tooth gels and tooth powders. Components of such toothpaste and tooth gels generally include one or more of a dental abrasive (from about 10% to about 50%), a surfactant (from about 0.5% to about 10%), a thickening agent (from about 0.1% to about 5%), a flavoring agent (from about 0.04% to about 2%), a sweetening agent (from about 0.1% to about 3%), and water (from about 2% to about 45%). Such toothpaste or tooth gel may also include one or more of an anticaries agent (from about 0.05% to about 0.3% as fluoride ion), and an anticalculus agent (from about 0.1% to about 13%). Tooth powders, of course, contain substantially all non-liquid components.

Other preferred compositions of the subject invention are mouthwashes, including mouth sprays. Components of such mouthwashes and mouth sprays typically include one or more of water (from about 45% to about 98%), a surfactant (from about 0.01% to about 7%), a flavoring agent (from about 0.04% to about 2%), and a sweetening agent (from about 0.1% to about 3%). Such mouthwashes and mouth sprays may also include one or more of an anticaries agent (from about 0.05% to about 0.3% as fluoride ion), and an anticalculus agent (from about 0.1% to about 3%).

Other preferred compositions of the subject invention are dental solutions including irrigation fluids. Components of such dental solutions generally include one or more of water (from about 90% to about 99%), preservative (from about 0.01% to about 0.5%), thickening agent (from 0% to about 5%), flavoring agent (from about 0.04% to about 2%), sweetening agent (from about 0.1% to about 3%), and surfactant (from 0% to about 5%).

Chewing gum compositions typically include one or more of a gum base (from about 15% to about 99%), a flavoring agent (from about 0.4% to about 4%) and a sweetening agent (from about 0.01% to about 20%).

The term "lozenge" as used herein includes: breath mints, troches, pastilles, microcapsules, and fast-dissolving solid forms including freeze dried forms (cakes, wafers, thin films, tablets) and fast-dissolving solid forms including compressed tablets. The term "fast-dissolving solid form" as used herein means that the solid dosage form dissolves in less than about 60 seconds, preferably less than about 15 seconds, more preferably less than about 5 seconds, after placing the solid dosage form in the oral cavity. Fast-dissolving solid forms are disclosed in WO 95/33446, published Dec. 14, 1995, Brideau; U.S. Pat. No. 4,642,903; U.S. Pat. No. 4,946,684; U.S. Pat. No. 4,305,502; U.S. Pat. No. 4,371,516; U.S. Pat. No. 5,188,825; U.S. Pat. No. 5,215,756; U.S. Pat. No. 5,298,261; U.S. Pat. No. 3,882,228; U.S. Pat. No. 4,687,662; U.S. Pat. No. 4,642,903.

Lozenges include discoid-shaped solids comprising a therapeutic agent in a flavored base. The base may be a hard sugar candy, glycerinated gelatin or combination of sugar with sufficient mucilage to give it form. These dosage forms are generally described in Remington: *The Science and Practice of Pharmacy*, 19$^{th}$ Ed., Vol. II, Chapter 92, 1995. Lozenge compositions (compressed tablet type) typically include one or more fillers (compressible sugar), flavoring agents, and lubricants. Microcapsules of the type contemplated herein are disclosed in U.S. Pat. No. 5,370,864, issued Dec. 6, 1994 to Peterson et al.

In still another aspect, the invention comprises a dental implement impregnated with a chlorite ion composition. The dental implement comprises an implement for contact with teeth and other tissues in the oral cavity, said implement being impregnated with a safe and therapeutically effective amount of chlorite ion. The dental implement can be impregnated fibers including dental floss or tape, chips or strips and polymer fibers. Dental floss or tape typically comprise from 0.01 mg to 0.1 mg chlorite ion per cm of material. The dental implement can also be a dental tool used for stimulating the periodontal tissue such as a toothpick or rubber-tip.

Types of carriers or oral care excipients which may be included in compositions of the present invention, along with specific non-limiting examples, are:

Abrasives

Dental abrasives useful in the topical, oral carriers of the compositions of the subject invention include many different materials. The material selected must be one, which is compatible within the composition of interest and does not excessively abrade dentin. Suitable abrasives include, for example, silicas including gels and precipitates, insoluble sodium polymetaphosphate, hydrated alumina, calcium carbonate, dicalcium orthophosphate dihydrate, calcium pyrophosphate, tricalcium phosphate, calcium polymetaphosphate, and resinous abrasive materials such as particulate condensation products of urea and formaldehyde.

Another class of abrasives for use in the present compositions is the particulate thermo-setting polymerized resins as described in U.S. Pat. No. 3,070,510 issued to Cooley & Grabenstetter on Dec. 25, 1962. Suitable resins include, for example, melamines, phenolics, ureas, melamine-ureas, melamine-formaldehydes, urea-formaldehyde, melamine-urea-formaldehydes, cross-linked epoxides, and cross-linked polyesters. Mixtures of abrasives may also be used.

Silica dental abrasives of various types are preferred because of their unique benefits of exceptional dental cleaning and polishing performance without unduly abrading tooth enamel or dentine. The silica abrasive polishing materials herein, as well as other abrasives, generally have an average particle size ranging between about 0.1 to about 30 microns, and preferably from about 5 to about 15 microns. The abrasive can be precipitated silica or silica gels such as the silica xerogels described in Pader et al., U.S. Pat. No. 3,538,230, issued Mar. 2, 1970, and DiGiulio, U.S. Pat. No. 3,862,307, issued Jan. 21, 1975. Preferred are the silica xerogels marketed under the trade name "Syloid" by the W. R. Grace & Company, Davison Chemical Division. Also preferred are the precipitated silica materials such as those marketed by the J. M. Huber Corporation under the trade name, Zeodent®, particularly the silica carrying the designation Zeodent 119®. The types of silica dental abrasives useful in the toothpastes of the present invention are described in more detail in Wason, U.S. Pat. No. 4,340,583, issued Jul. 29, 1982. The abrasive in the toothpaste compositions described herein is generally present at a level of from about 6% to about 70% by weight of the composition. Preferably, toothpastes contain from about 10% to about 50% of abrasive, by weight of the composition.

Another preferred precipitated silica is the silica disclosed in U.S. Pat. No. 5,603,920, issued on Feb. 18, 1997; U.S. Pat. No. 5,589,160, issued Dec. 31, 1996; U.S. Pat. No. 5,658,553, issued Aug. 19, 1997; U.S. Pat. No. 5,651,958, issued Jul. 29, 1997, all of which are assigned to the Procter & Gamble Co.

Mixtures of abrasives can be used. The total amount of abrasive in dentifrice compositions of the subject invention preferably range from about 6% to about 70% by weight; toothpastes preferably contain from about 10% to about 50% of abrasives, by weight of the composition. Solution, mouth spray, mouthwash and non-abrasive gel compositions of the subject invention typically contain no abrasive.

Surfactants (Sudsing Agents)

The present compositions may also comprise surfactants, also commonly referred to as sudsing agents. Suitable surfactants are those which are reasonably stable and foam throughout a wide pH range. The surfactant may be anionic, nonionic, amphoteric, zwitterionic, cationic, or mixtures thereof.

Anionic surfactants useful herein include the water-soluble salts of alkyl sulfates having from 8 to 20 carbon atoms in the alkyl radical (e.g., sodium alkyl sulfate) and the water-soluble salts of sulfonated monoglycerides of fatty acids having from 8 to 20 carbon atoms. Sodium lauryl sulfate and sodium coconut monoglyceride sulfonates are examples of anionic surfactants of this type. Other suitable anionic surfactants are sarcosinates, such as sodium lauroyl sarcosinate, taurates, sodium lauryl sulfoacetate, sodium lauroyl isethionate, sodium laureth carboxylate, and sodium dodecyl benzenesulfonate. Mixtures of anionic surfactants can also be employed. Many suitable anionic surfactants are disclosed by Agricola et al., U.S. Pat. No. 3,959,458, issued May 25, 1976. The present composition typically comprises an anionic surfactant at a level of from about 0.025% to about 9%, preferably from about 0.05% to about 5%, and most preferably from about 0.1% to about 1%.

Nonionic surfactants which can be used in the compositions of the present invention can be broadly described as compounds produced by the condensation of alkylene oxide groups (hydrophilic in nature) with an organic hydrophobic compound which may be aliphatic or alkyl-aromatic in nature. Examples of suitable nonionic surfactants include poloxamers (sold under trade name Pluronic), polyoxyethylene, polyoxyethylene sorbitan esters (sold under trade name Tweens), fatty alcohol ethoxylates, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides, and mixtures of such materials.

The amphoteric surfactants useful in the present invention can be broadly described as derivatives of aliphatic secondary and tertiary amines in which the aliphatic radical can be a straight chain or branched and wherein one of the aliphatic substituents contains from about 8 to about 18 carbon atoms and one contains an anionic water-solubilizing group, e.g., carboxylate, sulfonate, sulfate, phosphate, or phosphonate. Among suitable amphoteric surfactants are betaines, specifically cocamidopropyl betaine. Mixtures of amphoteric surfactants can also be employed. Many of these suitable nonionic and amphoteric surfactants are disclosed in U.S. Pat. No. 3,988,433 to Benedict and U.S. Pat. No. 4,051,234, issued Sep. 27, 1977 to Gieske et al.

The present composition can typically comprise a nonionic, amphoteric, or combination of nonionic and amphoteric surfactant each at a level of from about 0.025% to about 5%, preferably from about 0.05% to about 4%, and most preferably from about 0.1% to about 3%.

Fluoride Ions

The present compositions may also incorporate free fluoride ions. Preferred free fluoride ions can be provided by sodium fluoride, stannous fluoride, indium fluoride, and sodium monofluorophosphate. Sodium fluoride is the most preferred free fluoride ion. Norris et al., U.S. Pat. No. 2,946,725, issued Jul. 26, 1960, and Widder et al., U.S. Pat. No. 3,678,154 issued Jul. 18, 1972, disclose such salts as well as other salts.

The present compositions may contain from about 50 ppm to about 3500 ppm, and preferably from about 500 ppm to about 3000 ppm of free fluoride ions.

Thickening Agents

In preparing toothpaste or gels, it is necessary to add some thickening material to provide a desirable consistency of the composition, to provide desirable chlorite release characteristics upon use, to provide shelf stability, and to provide stability of the composition, etc. Examples of thickening agents are carboxyvinyl polymers, carrageenan, hydroxyethyl cellulose, laponite, powdered polyethylene and water soluble salts of cellulose ethers such as sodium carboxymethylcellulose and sodium carboxymethyl hydroxyethyl cellulose. Natural gums such as gum karaya, xanthan gum, gum arabic, and gum tragacanth can also be used. Colloidal magnesium aluminum silicate or finely divided silica can be used as part of the thickening agent to further improve texture.

A preferred class of thickening or gelling agents includes a class of homopolymers of acrylic acid crosslinked with an alkyl ether of pentaerythritol or an alkyl ether of sucrose, or carbomers. Carbomers are commercially available from B. F. Goodrich as the Carbopol®) series. Particularly preferred Carbopols include Carbopol 934, 940, 941, 956, and mixtures thereof. Other preferred thickening agents are polymeric polyether compounds, e.g., polyethylene or polypropylene oxide (M.W. 300 to 1,000,000), capped with alkyl or acyl groups containing 1 to about 18 carbon atoms, When chlorite is formulated separately in a dual phase composition, preferred thickening agents are hydroxyethyl cellulose and water-soluble salts of cellulose ethers such as sodium carboxymethyl cellulose and sodium carboxymethyl hydroxyethyl cellulose.

Thickening agents in an amount from about 0.1% to about 15%, preferably from about 2% to about 10%, more preferably from about 4% to about 8%, by weight of the total toothpaste or gel composition, can be used. Higher concentrations can be used for chewing gums, lozenges (including breath mints), sachets, non-abrasive gels and subgingival gels.

Humectants

Another optional component of the topical, oral carriers of the compositions of the subject invention is a humectant. The humectant serves to keep toothpaste compositions from hardening upon exposure to air, to give compositions a moist feel to the mouth, and, for particular humectants, to impart desirable sweetness of flavor to toothpaste compositions. The present compositions, however, preferably do not contain a humectant in the same aqueous phase as chlorite, as many of the conventional humectants cause some degradation of chlorite at typical levels used for aqueous formulations such as dentifrice and rinse. Examples of humectants that are preferably not formulated in the same aqueous phase as chlorite include polyhydric alcohols such as glycerin, sorbitol, xylitol, butylene glycol, polyethylene glycol, and propylene glycol. Humectants may be included in the non-chlorite containing phase of dual- or multi-phase aqueous formulations. Humectants may also be included in compositions that are substantially dry or contain minimal amounts of water such as tooth powders, lozenges and chewing gum, particularly if the chlorite is physically separated from the humectants, such as by microencapsulation.

Flavoring and Sweetening Agents

Flavoring agents can also be added to the compositions. Suitable flavoring agents are those that are stable and do not degrade in the presence of chlorite. It is particularly important for oral care compositions that the flavor components do not degrade resulting in changes in flavor quality and/or intensity, since consumer acceptance is highly influenced by the flavor of the product. Preferred flavor agents include menthol, menthone, dihydroanethole, eucalyptol, menthyl acetate and mixtures thereof. Synthetic flavoring agents are preferred over natural isolates since these isolates may contain reactive impurities that could be detrimental to stability. The terms menthol and menthyl as used herein include dextro- and levorotatory isomers of these compounds and racemic mixtures thereof. Flavoring agents are generally used in the compositions at levels of from about 0.001% to about 5%, by weight of the composition.

Suitable sweetening agents likewise should be stable and not degrade in the presence of chlorite. Preferred sweetening agents for use in the present compositions are saccharin, saccharin salts especially sodium saccharin, sucralose, and mixtures thereof. The compositions may comprise from about 0.1% to about 10% of these agents, preferably from about 0.1% to about 1%, by weight of the composition.

In addition to the flavoring and sweetening agents above, coolants can be used as optional ingredients in compositions of the present invention as long as they are compatible with chlorite and will not cause stability problems. These agents are present in the compositions at a level of from about 0.001% to about 10%, preferably from about 0.1% to about 1%, by weight of the composition. The coolant can be any of a wide variety of materials. Included among such materials are carboxamides and menthol. Preferred coolants in the present compositions are synthetic menthol and the paramenthan carboxyamide agents such as N-ethyl-p-menthan-3-carboxamide, known commercially as "WS-3", N,2,3-trimethyl-2-isopropylbutanamide, known as "WS-23," and mixtures thereof.

Anticalculus Agent

The present compositions may also include an anticalculus agent, preferably a pyrophosphate ion source such as pyrophosphate salts. The pyrophosphate salts useful in the present compositions include the dialkali metal pyrophosphate salts, tetraalkali metal pyrophosphate salts, and mixtures thereof. Disodium dihydrogen pyrophosphate ($Na_2H_2P_2O_7$), tetrasodium pyrophosphate ($Na_4P_2O_7$), and tetrapotassium pyrophosphate ($K_4P_2O_7$) in their unhydrated as well as hydrated forms are the preferred species. In the present compositions, the pyrophosphate salt may be present in one of three ways: predominately dissolved, predominately undissolved, or a mixture of dissolved and undissolved pyrophosphate.

Compositions comprising predominately dissolved pyrophosphate refer to compositions where at least one pyrophosphate ion source is in an amount sufficient to provide at least about 1.0% free pyrophosphate ions. The amount of free pyrophosphate ions may be from about 1% to about 15%, preferably from about 1.5% to about 10%, and most preferably from about 2% to about 6%. Free pyrophosphate ions may be present in a variety of protonated states depending on the pH of the composition.

Compositions comprising predominately undissolved pyrophosphate refer to compositions containing no more than about 20% of the total pyrophosphate salt dissolved in the composition, preferably less than about 10% of the total pyrophosphate dissolved in the composition. Tetrasodium pyrophosphate salt is the preferred pyrophosphate salt in these compositions. Tetrasodium pyrophosphate may be the anhydrous salt form or the decahydrate form, or any other species stable in solid form in the dentifrice compositions. The salt is in its solid particle form, which may be its crystalline and/or amorphous state, with the particle size of the salt preferably being small enough to be aesthetically acceptable and readily soluble during use. The amount of pyrophosphate salt useful in making these compositions is any tartar control effective amount, and is generally from about 1.5% to about 15%, preferably from about 2% to about 10%, and most preferably from about 3% to about 8%, by weight of the dentifrice composition.

Compositions may also comprise a mixture of dissolved and undissolved pyrophosphate salts. Any of the above mentioned pyrophosphate salts may be used.

The pyrophosphate salts are described in more detail in *Kirk-Othmer Encyclopedia of Chemical Technology,* Third Edition, Volume 17, Wiley-Interscience Publishers (1982).

Optional agents to be used in place of or in combination with the pyrophosphate salt include such known materials as synthetic anionic polymers, including polyacrylates and polyphosphates (e.g., tripolyphosphate), and mixtures thereof.

Alkali Metal Bicarbonate Salt

The present invention may also include an alkali metal bicarbonate salt. Alkali metal bicarbonate salts are soluble in water and unless stabilized, tend to release carbon dioxide in an aqueous system. Sodium bicarbonate, also known as baking soda, is the preferred alkali metal bicarbonate salt. The present composition may contain from about 0.1% to about 15%, and more preferably from about 0.2% to about 1% of an alkali metal bicarbonate salt.

Miscellaneous Carriers

Water employed in the preparation of commercially suitable oral compositions should preferably be of low ion content and free of organic impurities. Water can comprise up to about 98% particularly for mouth rinses, and preferably from about 5% to about 50%, by weight of the aqueous compositions herein. These amounts of water include the free water which is added plus that which is introduced with other materials. Compositions such as tooth powders, lozenges and chewing gum, are of course substantially dry or only contain a small amount of water. Mineral oil is another carrier that may be used in preparing oral compositions that are substantially non-aqueous or in combination with water in aqueous compositions.

The compositions of the present invention are preferably essentially free of peroxy compounds and of organic solvents. However, ethanol may be used in the compositions at low levels up to about 10% when in the same phase as chlorite. Higher levels of ethanol may be used in the non-chlorite containing phase of dual-phase formulations.

Agents for adjusting the pH of the compositions may also be used. Suitable for use in the present compositions are sodium hydroxide, sodium carbonate and sodium bicarbonate as required to reach the target alkaline pH.

Titanium dioxide may also be added to the present composition. Titanium dioxide is a white powder, which adds opacity to the compositions. Titanium dioxide generally comprises from about 0.25% to about 5% by weight of the dentifrice compositions.

Composition Use

A safe and effective amount of the compositions of the present invention and/or chlorite ion may be topically applied to the mucosal tissue of the oral cavity, to the gingival tissue of the oral cavity, and/or to the surface of the teeth, for the treatment or prevention of the above mentioned diseases or conditions of the oral cavity, in several conventional ways. For example, the gingival or mucosal tissue may be rinsed with a solution (e.g., mouth rinse, mouth spray) containing chlorite ion; or if chlorite ion is included in a dentifrice (e.g., toothpaste, tooth gel or tooth powder), the gingival/mucosal tissue or teeth is bathed in the liquid and/or lather generated by brushing the teeth. Other non-limiting examples include applying a non-abrasive gel or paste, which contains chlorite ion, directly to the gingival/mucosal tissue or to the teeth with or without an oral care appliance described below; chewing gum that contains chlorite; chewing or sucking on a breath tablet or lozenge which contains chlorite ion. Preferred methods of applying chlorite ion to the gingival/mucosal tissue and/or the teeth are via rinsing with a mouth rinse solution and via brushing with a dentifrice. Other methods of topically applying chlorite ion to the gingival/mucosal tissue and the surfaces of the teeth are apparent to those skilled in the art.

The concentration of chlorite ion in the composition of the present invention depends on the type of composition (e.g., toothpaste, mouth rinse, lozenge, gum, etc.) used to apply the chlorite ion to the gingival/mucosal tissue and/or the teeth, due to differences in efficiency of the compositions contacting the tissue and teeth, and due also to the amount of the composition generally used. The concentration may also depend on the disease or condition being treated.

It is preferred that the mouth rinse to be taken into the oral cavity have a concentration of chlorite ion in the range of from about 0.02% to about 0.5%, with from about 0.10% to about 0.30% by weight of the composition, even more preferred. Preferably mouth rinse compositions of the present invention deliver about 3.75 to about 30.0 mg of chlorite ion to the oral cavity when approximately 15 ml of the rinse is used.

Mouth sprays preferably have chlorite ion concentrations from about 0.15% to about 5%, with from about 0.2% to about 4% more preferred, with from about 0.5% to about 3.5%, by weight of the composition, even more preferred.

Preferably for dentifrices (including toothpaste and tooth gels) and non-abrasive gels, the concentration of chlorite ion is in the range of from about 0.5% to about 3.0%, by weight of the composition.

Chewing gums and lozenges (including breath mints), are generally formulated into compositions of individual unit size preferably containing from about 0.1 mg to about 12 mg, preferably from about 1 mg to about 6 mg, of chlorite ion, per unit used in the oral cavity (i.e., per stick of gum, lozenge, breath mint, etc.).

It should be understood that the present invention relates not only to methods for delivering the present chlorite containing compositions to the oral cavity of a human, but also to methods of delivering these compositions to the oral cavity of other animals, e.g., household pets or other domestic animals, or animals kept in captivity. Other animals include for example, dogs, cats or horses.

Pet care products such as foods, chews and toys are generally formulated to contain from 0.2 mg to 200 mg chlorite per unit of product to be administered to the animal. The chlorite can be incorporated for example, into a relatively supple but strong and durable material such as rawhide, ropes made from natural or synthetic fibers, and polymeric articles made from nylon, polyester or thermoplastic polyurethane. As the animal chews, licks or gnaws the product, chlorite and any other incorporated active elements are released into the animal's oral cavity into a salivary medium, comparable to an effective brushing or rinsing. Pet food embodiments can be formulated to provide from 0.2 mg to 200 mg chlorite per feeding or treating session. The chlorite can be incorporated as an ingredient or ad mixed into a pet food such as for example, a kibbled, semi-moist, or canned food. Highly preferred food embodiments include carriers that tend to increase residence time of the food in the oral cavity. For example, the chlorite can be incorporated in a carrier that will stick or adhere to the teeth, in order that a certain amount of product will remain in the mouth and not be ingested immediately. The present chlorite compositions may also be incorporated into other pet care products, including nutritional supplements and drinking water additives.

For dual- or multi-phase compositions the above concentrations of chlorite ion represent the concentration of chlorite ion after the phases are mixed together, which is usually just prior to use by the consumer. Thus, the concentration of chlorite ion in the chlorite containing phase will vary depending on the amount of the second or additional phases to be mixed with the chlorite-containing phase to obtain the final product for use.

For the method of treating diseases or conditions of the oral cavity, including breath malodor (as well as long lasting breath protection), a safe and effective amount of chlorite ion is preferably applied to the gingival/mucosal tissue and/or the teeth (for example, by rinsing with a mouthrinse, directly applying a non-abrasive gel with or without a device, applying a dentifrice or a tooth gel with a toothbrush, sucking or chewing a lozenge or breathmint, etc.) preferably for at least about 10 seconds, preferably from about 20 seconds to about 10 minutes, more preferably from about 30 seconds to about 60 seconds. The method often involves expectoration of most of the composition following such contact. The frequency of such contact is preferably from about once per week to about four times per day, more preferably from about thrice per week to about three times per day, even more preferably from about once per day to about twice per day. The period of such treatment typically ranges from about one day to a lifetime. For particular oral care diseases or conditions the duration of treatment depends on the severity of the oral disease or condition being treated, the particular delivery form utilized and the patient's response to treatment. If delivery to the periodontal pockets is desirable, such as with the treatment of periodontal disease, a mouthrinse can be delivered to the periodontal pocket using a syringe or water injection device. These devices are known in the art and include "Water Pik" by Teledyne Corporation. After irrigating, the subject can swish the rinse in the mouth to also cover the dorsal tongue and other gingival and mucosal surfaces. In addition a toothpaste, non-abrasive gel, toothgel, etc. can be brushed onto the tongue surface and other gingival and mucosal tissues of the oral cavity.

The present compositions may also be delivered to tissues and/or spaces within the oral cavity using electromechanical devices such as metering devices, targeted application devices and cleaning or integrated oral hygiene systems.

For treating oral tissue wounds and aiding tissue regeneration, fluid subgingival gel compositions that can be inserted via syringe and either a needle or catheter directly into the areas needing treatment, such as the periodontal cavities, are very useful and convenient. Preferred gel-like fluid compositions are those that transform into near solid phase in the presence of aqueous fluid such as water or crevicular fluid. The hardened composition is thus retained at the site of application, and the chlorite and any other active agent continue to release in a sustained manner from such compositions.

The following examples further describe and demonstrate embodiments within the scope of the present invention. These examples are given solely for the purpose of illustration and are not to be construed as limitations of the present invention as many variations thereof are possible without departing from the spirit and scope.

All percentages used herein are by weight of the composition unless otherwise indicated.

EXAMPLES

Example 1

Dual Phase Dentifrice

| Non-Chlorite Phase | | Chlorite Phase | |
|---|---|---|---|
| Ingredient | Wt. % | Ingredient | Wt. % |
| Sorbitol (70% Solution) | 5.600 | Sodium Chlorite (80%) | 3.750 |
| Glycerin | 9.000 | Laponite | 4.500 |
| Propylene Glycol | 6.000 | Na Carboxymethyl cellulose | 1.500 |
| Sodium Fluoride | 0.486 | | |
| Sodium Carbonate | 1.000 | Xanthan Gum | 0.500 |
| Sodium Bicarbonate | 20.000 | Sodium Carbonate | 0.530 |
| Precipitated Silica | 20.000 | Sodium Bicarbonate | 0.420 |
| Xanthan Gum | 0.500 | Sodium Hydroxide | 0.130 |
| Sodium Carboxymethyl Cellulose | 0.400 | Purified Water | QS |
| Sodium alkyl sulfate (27.9% Sol'n) | 8.000 | Chlorite phase pH = approximately 10 | |
| Titanium Dioxide | 0.700 | | |
| Sodium Saccharin | 0.350 | | |
| Flavor | 2.000 | | |
| Poloxamer 407 | 2.000 | | |
| Purified Water and minors | QS | | |

Example 2

Dual Phase Dentifrice

| Non-Chlorite Phase | | Chlorite Phase | |
|---|---|---|---|
| Ingredient | Wt. % | Ingredient | Wt. % |
| Sorbitol (70% Solution) | 7.820 | Sodium Chlorite (80%) | 3.120 |
| Glycerin | 9.000 | Carbomer | 3.900 |
| Propylene Glycol | 6.000 | Sodium Bicarbonate | 0.840 |
| Polyethylene Glycol 600 | 2.000 | Sodium Hydroxide | 3.900 |
| Sodium Fluoride | 0.486 | Purified Water | QS |
| Precipitated Silica | 30.000 | Chlorite phase pH = approximately 10 | |
| Xanthan Gum | 0.500 | | |
| Sodium Carboxymethyl Cellulose | 0.400 | | |
| Sodium alkyl sulfate (27.9% Sol'n) | 8.000 | | |
| Titanium Dioxide | 0.700 | | |
| Sodium Saccharin | 0.600 | | |
| Flavor | 2.000 | | |
| Sodium Carbonate | 0.500 | | |
| Sodium Bicarbonate | 8.000 | | |
| Purified Water and minors | QS | | |

Making Procedure

The dual-phase dentifrices of Examples 1 and 2 are prepared as follows:

Chlorite Phase
1) Add water to mixing vessel.
2) Add thickener (Carbomer or laponite/Na carboxymethyl cellulose/xanthan gum) to vessel with mixing.
3) Adjust pH to approximately 10 with sodium hydroxide.
4) Add Na chlorite and Na bicarbonate with mixing.

Non-Chlorite Phase
1) Add water and sorbitol to mixing vessel.
2) Add sodium fluoride and Na saccharin to vessel with mixing.
3) Disperse Na carboxymethyl cellulose and xanthan gum in glycerin and add dispersion to vessel with mixing.
4) Add propylene glycol, polyethylene glycol, poloxamer, sodium carbonate, Na lauryl sulfate solution, flavor concentrate, titanium dioxide and silica to vessel with mixing.
5) Add sodium bicarbonate to vessel with mixing.

Example 3

Single Phase Dentifrice

| Ingredient | 3A Wt. % | 3B Wt. % | 3C Wt. % | 3D Wt. % | 3E Wt. % | 3F Wt. % | 3G Wt. % |
|---|---|---|---|---|---|---|---|
| Sodium Chlorite (80%) | 0.625 | 3.750 | 1.875 | 3.750 | 1.875 | 3.750 | 2.500 |
| Sodium Fluoride | 0.243 | 0.243 | 0.243 | 0.243 | 0.243 | 0.243 | 0.243 |
| Silica - Zeodent 119 | 20.000 | 20.000 | 20.000 | 20.000 | 20.000 | — | — |
| Silica - Zeodent 118 | — | — | — | — | — | — | 31.000 |
| Calcium Pyrophosphate | — | — | — | — | — | 39.750 | — |
| Sodium Bicarbonate | 0.840 | 0.840 | 0.210 | 0.840 | — | — | 0.420 |
| Sodium Hydroxide | 3.150 | 3.150 | 3.150 | 3.150 | 0.900 | 0.125 | 3.450 |
| Tetrapotassium Pyrophosphate (59.9%) | — | — | — | 6.350 | — | — | 5.045 |
| Sodium Alkyl Sulfate (27.9% Sol'n) | 4.000 | 4.000 | 4.000 | 4.000 | — | — | 4.000 |
| Sodium Alkyl Sulfate Powder | — | — | — | — | 2.000 | 2.000 | — |
| Titanium Dioxide | — | — | — | — | 0.500 | — | — |
| Menthol | 0.350 | 0.350 | 0.175 | 0.350 | 0.770 | 0.770 | — |
| N-ethyl-p-menthan-3-carboxamide | 0.075 | 0.075 | 0.038 | 0.075 | 0.165 | 0.165 | — |
| N,2,3-trimethyl-2-isopropylbutanamide | 0.075 | 0.075 | 0.038 | 0.075 | 0.165 | 0.165 | — |

-continued

| Ingredient | 3A Wt. % | 3B Wt. % | 3C Wt. % | 3D Wt. % | 3E Wt. % | 3F Wt. % | 3G Wt. % |
|---|---|---|---|---|---|---|---|
| Sodium Saccharin | 0.520 | 0.520 | 0.520 | 0.520 | 1.000 | 1.000 | 0.300 |
| Flavor* | — | — | — | — | — | — | 0.575 |
| Carbopol | 1.000 | 1.000 | 1.000 | 1.000 | — | — | 0.500 |
| Sodium Carboxymethyl-cellulose | 1.500 | 1.500 | 1.500 | 1.500 | — | — | 0.500 |
| Powdered Polyethylene | — | — | — | — | 20.000 | 15.000 | — |
| Mineral Oil and minors | — | — | — | — | QS | QS | — |
| Purified Water and minors | QS | QS | QS | QS | — | — | QS |

*Flavor containing eucalyptol, menthone, menthol, dihydroanethole, WS-3 and WS-23

Making Procedure

The aqueous based dentifrice formulations (Examples 3A-3D and 3G) are prepared as follows:

1) Add water to mixing vessel.
2) Dry mix carbopol, Na carboxymethyl cellulose with ½ of the silica and slowly add to vessel with mixing.
3) Add Na hydroxide and Na bicarbonate with mixing.
4) Add Na lauryl sulfate solution, Na saccharin, fluoride, flavor components and tetrasodium pyrophosphate with mixing.
5) Adjust pH to approximately 10.
6) Add Na chlorite with mixing.

The mineral oil based dentifrice formulations (Examples 3E and 3F) are prepared as follows:

1) Add mineral oil to mixing vessel and heat.
2) Add a portion of the polyethylene powder and dissolve in the heated mineral oil. Start cooling the mixture. Dry mix carbopol, Na carboxymethyl cellulose with ½ of the silica and slowly add to vessel with mixing.
3) Add abrasive (silica/calcium pyrophosphate), Na lauryl sulfate powder, Na hydroxide, remaining polyethylene powder, Na saccharin, fluoride, and flavor concentrate with mixing.
4) Add Na chlorite with mixing.

Example 4

Dual Phase Rinse

| Non-Chlorite Phase | | Chlorite Phase | |
|---|---|---|---|
| Ingredient | Wt. % | Ingredient | Wt. % |
| Glycerin | 14.980 | Sodium Chlorite (80%) | 0.500 |
| Sodium Benzoate | 0.107 | Sodium Carbonate | 0.290 |
| Benzoic Acid | 0.009 | Sodium Bicarbonate | 0.192 |
| Polysorbate 80 | 0.200 | Purified Water | QS |
| Sodium Saccharin | 0.240 | | |
| Peppermint Flavor | 0.500 | | |
| Ethanol | 29.970 | | |
| Purified Water, FD&C Blue #1 and minors | QS | | |

Making Procedure

The dual-phase rinse of Example 4 is prepared as follows:

Chlorite Phase

1) Add water to mixing vessel.
2) Add sodium carbonate and sodium bicarbonate to vessel with mixing.
3) Adjust pH to approximately 10.
4) Add Na chlorite with mixing.

Non-Chlorite Phase

1) Add water, glycerin, Polysorbate and ethanol to vessel with mixing.
2) Add and mix remaining components.

Example 5

Single Phase Rinse

| Component | 5A % W/W | 5B % W/W |
|---|---|---|
| Ethanol | 1.1185 | — |
| Sodium Carbonate | 0.2900 | 0.2900 |
| Sodium Bicarbonate | 0.1920 | 0.1920 |
| Poloxamer 407 | 0.5395 | 0.5395 |
| Sodium Lauryl Sulfate Solution (27.9% W/W) | 0.3150 | 0.3150 |
| Sodium Carboxymethyl Cellulose | 0.2000 | 0.2000 |
| Sodium Saccharin | 0.0600 | 0.0600 |
| Menthol | 0.0200 | 0.0200 |
| WS-3 (N-Ethyl-p-Menthan-3-Carboxamide) | 0.0100 | 0.0100 |
| WS-23 (N, 2, 3-trimethyl-2-2isopropyl butamide) | 0.0100 | 0.0100 |
| Sodium Chlorite (80% powder) | 0.2500 | 0.2500 |
| Water | QS | QS |

Making Procedure

The single phase rinse compositions of Example 5 are prepared as follows:

1) Add water to mixing vessel.
2) Add the Poloxamer to vessel with mixing.
3) Mix the ethanol and flavor concentrate (consisting of menthol, WS-3, WS-23, Na lauryl sulfate, water, and minor amounts of Poloxamer and ethanol) and add slowly to vessel with mixing.
4) Dry mix Na carboxymethyl cellulose, with Na saccharin, Na carbonate, and Na bicarbonate, and add to the vessel with mixing.
5) Adjust pH to approximately 10.
6) Add Na chlorite with mixing.

Example 6

Non-Abrasive Gel (With Flavor)

| Component | % W/W |
|---|---|
| Sodium Bicarbonate | 0.210 |
| Sodium Carbonate | 0.266 |

-continued

| Component | % W/W |
|---|---|
| Carbomer | 3.000 |
| Sodium Chlorite 80% Powder | 0.838 |
| Sodium Saccharin | 0.400 |
| Menthol | 0.350 |
| Menthone | 0.050 |
| Eucalyptol | 0.020 |
| Dihydroanethole | 0.005 |
| N-Ethyl-p-Menthan-3-Carboxamide (WS-3) | 0.075 |
| N,2,3-trimethyl-2-2isopropyl butamide (WS-23) | 0.075 |
| Sodium Hydroxide | QS |
| Water and minors | QS |

Example 7

Non-Abrasive Gel (Without Flavor)

| Component | % W/W |
|---|---|
| Sodium Bicarbonate | 0.210 |
| Sodium Carbonate | 0.266 |
| Carbomer | 3.000 |
| Sodium Chlorite 80% Powder | 0.838 |
| Sodium Hydroxide | QS |
| Water | QS |

Making Procedure:

1) Add water to mixing vessel.
2) Slowly add Carbomer to water with mixing.
3) Adjust the pH to approximately 10 using sodium hydroxide.
4) Add the sodium bicarbonate, sodium saccharin, and flavor components (menthol, menthone, eucalyptol, dihydroanethole, WS-3, and WS-23) with mixing.
5) Add sodium chlorite with mixing.

Example 8

Oral Spray

| Component | % W/W |
|---|---|
| Sodium Carbonate | 0.290 |
| Sodium Bicarbonate | 0.192 |
| Poloxamer 407 | 0.750 |
| Sodium Carboxymethyl Cellulose | 0.200 |
| Sodium Saccharin | 0.400 |
| Sodium Chlorite (80% powder) | 0.838 |
| Menthol | 0.350 |
| Menthone | 0.050 |
| Eucalyptol | 0.020 |
| Dihydroanethole | 0.005 |
| N-Ethyl-p-Menthan-3-Carboxamide (WS-3) | 0.075 |
| N,2,3-trimethyl-2-2isopropyl butamide (WS-23) | 0.075 |
| Water | QS |

Making Procedure:

The oral spray of Example 8 is prepared as follows:

1) Add water to mixing vessel.
2) Add the Poloxamer to vessel with mixing.
3) Mix ethanol and flavor concentrate (consisting of menthol, menthone, eucalyptol, dihydroanethole, WS-3, WS-23, water, and minor amounts of Poloxamer and ethanol) and add slowly to vessel with mixing.
5) Dry mix sodium carboxymethyl cellulose, with sodium saccharin, sodium carbonate, and sodium bicarbonate, and add to the vessel with mixing.
6) Adjust pH to approximately 10.
7) Add sodium chlorite with mixing.

Example 9

Pet Products

Chlorite-containing pet rawhide chips and toy ropes are prepared by spraying with the oral spray of Example 8 (10–20 ml per item). The impregnated items are given to dogs immediately or stored in sealed plastic bags to remain moist.

Stability Testing

Product samples were placed in appropriate containers and placed in storage at various temperature conditions: room temperature (25° C.), accelerated temperature condition (40° C.) and refrigerated temperature condition (5° C.). Product samples were monitored for chlorite concentration, pH (of neat aqueous product), formation of chlorine dioxide, and flavor changes initially and at various time intervals. Organoleptic assessments, gas chromatography analysis for flavor ingredients as well as chlorite analysis were conducted. Samples were also monitored for chlorine dioxide formation by odor and yellow color formation. Results of the stability testing are shown below. All formulations according to the present invention are stable under storage conditions, showing no significant loss in chlorite, no evidence of chlorine dioxide formation, no significant change in pH and no significant flavor component degradation or change in overall flavor acceptability. Organoleptic analysis revealed a change in the overall flavor character. The taste of the product had become more well-rounded with a milder flavor of acceptable quality and peppermint character. Individually, the flavors of menthone, menthyl acetate, and dihydroanethole (tested at twelve weeks) also changed slightly, but were still characteristic of the respective compounds. The mellowing of flavor and change in character is typical for aged product and not beyond the anticipated organoleptic result. Eucalyptol showed no change in character or impact.

Results of Stability Testing

| Product Sample | Temp. | Assay | Theoretical | 1 mo. | 2 mos. | 3 mos. | 6 mos. | 12 mos. |
|---|---|---|---|---|---|---|---|---|
| Ex. 3A dentifrice | 25° C. | chlorite | 0.50% | 0.54% | 0.54% | 0.57% | 0.54% | 0.55% |
| | 25° C. | pH | 10.0 | NR | 10.08 | 10.13 | 10.13 | 10.08 |
| | 40° C. | chlorite | 0.54% | NR | 0.54% | 0.56% | | |
| | 40° C. | pH | 10.0 | NR | 10.16 | 10.21 | | |
| Ex. 3B dentifrice | 25° C. | chlorite | 3.00% | 3.08% | 3.02% | 3.08% | 3.12% | 3.04% |
| | 25° C. | pH | 10.0 | NR | 9.88 | 9.91 | 9.94 | 9.86 |
| | 40° C. | chlorite | 3.00% | 3.04% | 3.01% | 3.04% | | |
| | 40° C. | pH | 10.0 | NR | 9.94 | 9.97 | | |
| Ex. 3C dentifrice | 25° C. | chlorite | 1.50% | 1.54% | 1.56% | 1.53% | 1.60% | 1.54% |
| | 25° C. | pH | 10.0 | 10.10 | 10.16 | 10.12 | 10.20 | 10.15 |
| | 40° C. | chlorite | 1.50% | 1.53% | 1.54% | 1.53% | | |
| | 40° C. | pH | 10.0 | 10.18 | 10.29 | 10.25 | | |
| Ex. 3D dentifrice | 25° C. | chlorite | 3.00% | 3.06% | 3.31% | 3.06% | 3.17% | 3.10% |
| | 25° C. | pH | 10.0 | 10.14 | 10.12 | 10.22 | 10.16 | 10.12 |
| | 40° C. | chlorite | 3.00 | 3.03% | 3.56% | 3.02% | | |
| | 40° C. | pH | 10.0 | 10.16 | 10.25 | 10.22 | | |
| Ex. 3E dentifrice | 25° C. | chlorite | 1.50% | NR | 1.55% | 1.57% | 1.60% | NR |
| | 40° C. | chlorite | 1.50% | NR | 1.44% | 1.56% | | |
| Ex. 3F dentifrice | 25° C. | chlorite | 3.00% | NR | 3.06% | 2.99% | 3.13% | NR |
| | 40° C. | chlorite | 3.00% | NR | 3.03% | 2.92% | | |
| Ex. 5A rinse | 25° C. | chlorite | 0.20% | 0.204% | NR | 0.204% | 0.197% | 0.212% |
| | 25° C. | pH | 10.0 | 9.96 | NR | 9.98 | 9.94 | 9.99 |
| | 40° C. | chlorite | 0.20% | 0.205% | NR | 0.200% | 0.199% | 0.207% |
| | 40° C. | pH | 10.0 | 9.96 | NR | 9.97 | 9.91 | 9.96 |
| Ex. 5B rinse | 25° C. | chlorite | 0.20% | 0.200% | NR | 0.200% | 0.196% | 0.207% |
| | 25° C. | pH | 10.0 | 9.97 | NR | 9.98 | 9.92 | 9.98 |
| | 40° C. | chlorite | 0.20% | 0.200% | NR | 0.199% | 0.198% | 0.203% |
| | 40° C. | pH | 10.0 | 9.96 | NR | 9.97 | 9.90 | 9.96 |
| Ex. 2 chlorite phase | 25° C. | chlorite | 2.50% | 2.44% | 2.49% | 2.45% | 2.64% | 2.68% |
| | 25° C. | pH | 10.0 | 10.24 | 10.35 | 10.26 | 10.44 | 10.18 |
| | 40° C. | chlorite | 2.50% | 2.44% | 2.50% | | | |
| | 40° C. | pH | 10.0 | 10.19 | 10.30 | | | |
| Ex. 1 chlorite phase | 25° C. | chlorite | 3.00% | 3.09% | NR | 2.99% | 3.23% | 3.07% |
| | 25° C. | pH | 10.0 | 10.0 | NR | 9.96 | 9.98 | 9.91 |
| | 40° C. | chlorite | 3.00% | 3.04% | NR | 3.00% | | |
| | 40° C. | pH | 10.0 | 9.90 | NR | 9.90 | | |
| Ex. 3G dentifrice | 5° C. | Chlorite | 2.00% | NR | NR | 2.082% | | |
| | 5° C. | Eucalyptol | 0.020% | 0.017% | 0.017% | 0.017% | | |
| | 5° C. | Menthone | 0.050% | 0.043% | 0.040% | 0.040% | | |
| | 5° C. | Menthol | 0.350% | 0.329% | 0.325% | 0.331% | | |
| | 5° C. | Dihydro-anethole | 0.005% | 0.004% | 0.004% | 0.004% | | |
| | 5° C. | WS-23 | 0.075% | 0.086% | 0.087% | 0.087% | | |
| | 5° C. | WS-3 | 0.075% | 0.081% | 0.080% | 0.080% | | |
| | 5° C. | Total flavor | 0.575% | 0.560% | 0.553% | 0.559% | | |
| | 40° C. | Chlorite | 2.00% | NR | NR | 1.998% | | |
| | 40° C. | Eucalyptol | 0.020% | 0.015% | 0.015% | 0.017% | | |
| | 40° C. | Menthone | 0.050% | 0.031% | 0.023% | 0.021% | | |
| | 40° C. | Menthol | 0.350% | 0.298% | 0.294% | 0.330% | | |
| | 40° C. | Dihydro-anethole | 0.005% | 0.004% | 0.003% | 0.004% | | |
| | 40° C. | WS-23 | 0.075% | 0.081% | 0.080% | 0.087% | | |
| | 40° C. | WS-3 | 0.075% | 0.071% | 0.071% | 0.079% | | |
| | 40° C. | Total flavor | 0.575% | 0.501% | 0.486% | 0.538% | | |

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An oral care composition for humans and other animals comprising:
   (a) from about 0.02% to about 6.0%, by weight of the final composition, of chlorite ion; and
   (b) a pharmaceutically-acceptable topical, chlorite-stable flavored oral carrier comprising solid or liquid excipients and diluents, which are capable of being commingled with chlorite without substantially interacting with chlorite in a manner which would substantially reduce the stability of the composition;
   wherein the composition is essentially free of chlorine dioxide or chlorous acid both tending to alter flavor and having an unpleasant taste; the pH of the final composition is greater than 7, and the composition is stable against loss of chlorite for a period of at least one year under normal storage conditions at about 25° C. or for a period of at least three months under accelerated storage conditions at about 40° C. said chlorite-stable oral care composition comprising a flavor system comprising one or a mixture of flavoring agents selected from menthol, eucalyptol, menthone, menthyl acetate, dihydroanethole, N-ethyl- o-menthan-3-carboxamide (WS-3), N,2,3-trimethyl-2-isopropylbutanamide (WS-23 and mixtures thereof with sweetening agents selected from saccharin and sucralose, said chlorite-satble flavor system being substantially free of chlorite-sensitive compounds that degrade in the presence of chlorite.

2. An oral care composition according to claim 1, in the form of a dentifrice paste or gel comprising from about 0.5% to about 3.0% chlorite by weight of the composition.

3. An oral care composition according to claim 1, in the farm of a mouthrinse comprising from about 0.075% to about 0.30% chlorite by weight of the composition.

4. An oral care composition according to claim 1, in the form of a lozenge or chewing gum comprising from about 0.1 mg to about 12 mg chlorite per unit of product.

5. An oral care composition according to claim 1, in the form of a mouth spray comprising from about 0.5% to about 3.5% chlorite by weight of the composition.

* * * * *